(12) United States Patent
Dunn et al.

(10) Patent No.: US 6,777,727 B2
(45) Date of Patent: Aug. 17, 2004

(54) FLEXURAL PLATE WAVE SYSTEMS (75) Inventors: Gregory J. Dunn, Arlington Heights, IL (US); Allyson Beuhler, Downers Grove, IL (US); David Penunuri, Fountain Hills, AZ (US)

(73) Assignee: Motorola, Inc., Schaumburg, IL (US)

( * ) Notice: Subject to any disclaimer, the term of this patent is extended or adjusted under 35 U.S.C. 154(b) by 2 days.

(21) Appl. No.: 10/304,429

(22) Filed: Nov. 26, 2002

(65) Prior Publication Data

US 2004/0101990 A1 May 27, 2004

(51) Int. Cl.[7] .................. H01L 29/80; H01L 31/112; H01L 31/0288
(52) U.S. Cl. ...................... 257/257; 257/431
(58) Field of Search .................. 257/257, 416, 257/431, 440, 444, 451

(56) References Cited

U.S. PATENT DOCUMENTS 6,510,597 B2 * 1/2003 Yoshida et al. ............ 29/25.35

* cited by examiner

Primary Examiner—Phuc T. Dang
(74) Attorney, Agent, or Firm—William E. Koch (57) ABSTRACT

An exemplary system and method for providing an acoustic plate wave apparatus is disclosed as comprising inter alia: a monocrystalline silicon substrate (200); an amorphous oxide material (220); a monocrystalline perovskite oxide material (230); a monocrystalline piezoelectric material (240); and a flexural plate wave component (250, 270) having an input interdigitated transducer (270), an output interdigitated transducer (250) and an optional support layer (260). Deposition or removal of material on or from an absorptive thin film sensor surface (210), or changes in the mechanical properties of the thin film (210) in contact with various chemical species, or changes in the electrical characteristics of a solvent solution exposed to the thin film (210) generally operate to produce measurable perturbations in the vector quantities (e.g., velocity, etc.) and scalar quantities (e.g., attenuation, etc.) of the acoustic plate modes.

17 Claims, 1 Drawing Sheet

FLEXURAL PLATE WAVE SYSTEMS

FIELD OF INVENTION

The present invention generally concerns acoustic wave devices and methods for their fabrication; and more particularly, in various representative and exemplary embodiments, to flexural plate wave micro-pumps, micro-filters and sensor elements having epitaxial PZT piezoelectric membranes.

BACKGROUND

For many years, attempts have been made to grow various monolithic thin films on foreign substrates such as silicon. To achieve optimal characteristics of various monolithic layers, however, a monocrystalline film of high crystalline quality is typically desired. Attempts have been made, for example, to grow various monocrystalline layers on a substrate such as germanium, silicon, and various insulators. These attempts have generally been unsuccessful due in part to lattice mismatches between the host crystal and the grown crystal causing the resulting layer of monocrystalline material to be of relatively low crystalline quality.

Acoustic plate wave devices have several applications in the microelectronics industry. For example, flexural plate wave devices may be used to perform active or passive signal processing functions suitable for delay lines, attenuators, phase shifters, filters, amplifiers, oscillators, mixers, limiters, and the like. Such devices are often connected to other microelectronics components such as integrated circuits and RF generators to form assemblies for telecommunication, digital processing as well as other applications.

Plate wave devices generally include a transducer coupled to piezoelectric material that converts an electronic signal received from the transducer to an acoustic plate wave. The plate modes generally consist of acoustic wave energy reflected back and forth between the faces of the piezoelectric plate while propagating along the length of the crystal. Flexural plate wave devices are often fabricated by forming the transducer on the surface of a piezoelectric material or over a substrate, which itself may or may not be piezoelectric.

Attempts have also been made to grow thin-films of piezoelectric material over a semiconductor substrate. Formation of such films on semiconductor substrates is desirable because it allows for the integration of acoustic wave devices with other microelectronics devices on a substantially unitary substrate. However, thin films of piezoelectric material formed on semiconductor substrates are of generally lesser quality than bulk piezoelectric material because lattice mismatches between the host crystal, or semiconductor substrate, and the grown crystal, or piezoelectric material, typically cause the grown thin film of piezoelectric material to be of relatively low crystalline quality. Furthermore, such thin films of piezoelectric material must generally be chosen from a set of materials that are generally compatible with the semiconductor substrate.

Moreover, the desirable characteristics of acoustic plate wave devices increase as the crystallinity of the piezoelectric film increases. For example, the electromechanical coupling coefficient and the piezoelectric coefficient of a piezoelectric material in monocrystalline form are typically higher than those of the same material in polycrystalline or amorphous form. If a large area thin film of high quality monocrystalline piezoelectric material were available at relatively low cost, a variety of flexural plate wave devices could advantageously be fabricated using such a film at relatively low cost compared to that of fabricating such devices on a bulk wafer of the piezoelectric material or on an epitaxial film of such material on, for example, a sapphire substrate. In addition, if thin films of high quality monocrystalline piezoelectric material and compound semiconductor material could be realized on a bulk wafer, such as a silicon wafer, an integrated device structure could be achieved that advantageously uses the properties of both the compound semiconductor material and the piezoelectric material. Modular technologies such as low temperature co-fired ceramic (LTCC) technologies can be adapted to combine diverse substrates, however the overall size of such devices generally may not be readily reduced, as compared to the aggregate size of discrete devices, due inter alia to interconnection requirements for wire bonding and the like. Accordingly, a need exists for a flexural plate wave system formed from high-quality, highly-ordered, monocrystalline piezoelectric material.

Acoustic waves (AW) in piezoelectric structures have been previously used to measure liquids in contact with piezoelectric structures. See, for example, U.S. Pat. No. 4,378,168 to Kuisma which discloses a piezoelectric device having spaced input and output electrodes on a surface for generating a surface acoustic wave (SAW) for detecting the presence of humidity between the electrodes as a function of signal attenuation.

The use of devices that employ Rayleigh waves (i.e., SAWs) to sense mass changes at solid/gas interfaces is also known; however, SAWs are generally impractical for use in sensor applications because Rayleigh waves typically do not propagate efficiently at solid-liquid interfaces. For example, Rayleigh waves generally have a surface-normal component of particle displacement which typically generates compressive waves in a liquid, thereby leading to substantial signal attenuation.

U.S. Pat. No. 4,691,714 to Wong et al. generally discloses the use of bulk acoustic waves within a piezoelectric structure to measure viscosity of a liquid in contact therewith. The viscosity of the liquid is described as a function of the amplitude of the transmitted bulk acoustic signal while the temperature of the liquid (i.e., the temperature of the sensing transducer) is a function of the phase of the SAW propagated in the device.

U.S. Pat. No. 5,117,146 to Martin et al. discloses solid-state acoustic sensors for monitoring conditions at a surface immersed in a liquid by placement of inter-digitated input and output transducers on a piezoelectric substrate with the propagation of acoustic plate modes therebetween, but does not enable, disclose or otherwise suggest structure and/or means for the fabrication of such a device from high-quality, highly-ordered, monocrystalline material.

U.S. Pat. No. 6,232,139 and WO Patent WO0171336 disclose the fabrication of plate wave devices employing sputter deposited AlN and ZnO layers.

More recent work has focused on employing polycrystalline lead zirconate titanate, which has a somewhat higher piezoelectric coefficient. All of this work, however, has been generally limited to polycrystalline piezoelectric films.

SUMMARY OF THE INVENTION

In various representative aspects, the present invention provides a system and method for providing flexural plate wave micropumps, microfilters, and/or sensor components comprising, for example, epitaxial PZT as a piezoelectric membrane. An exemplary system and method for providing an acoustic plate wave apparatus is disclosed as comprising inter alia: a monocrystalline silicon substrate; an amorphous oxide material layer; a monocrystalline perovskite oxide material layer; a monocrystalline piezoelectric material layer; and a flexural plate wave component having an input interdigitated transducer, an output interdigitated transducer and an optional support layer. Deposition or removal of material on or from an absorptive thin film sensor surface, or changes in the mechanical properties of the thin film upon making contact with various chemical species, or changes in the electrical characteristics of a solvent solution exposed to the thin film generally operate to produce measurable perturbations in the vector quantities (e.g., velocity, etc.) and scalar quantities (e.g., attenuation, etc.) of the acoustic plate modes.

When monolithically integrated with silicon or compound semiconductor devices, a representative design is disclosed as comprising highly miniaturized, self-contained sensing and analysis components with remote wireless monitoring capabilities; however, the disclosed system and method may be readily and more generally adapted for use in any plate wave driven system or application. For example, the present invention may embody a device and/or method for providing integrated pumping and/or valving systems for use in microfluidic, sensor, chromatographic or other partitioning applications. Additional advantages of the present invention will be set forth in the Detailed Description which follows and may be obvious from the Detailed Description or may be learned by practice of exemplary embodiments of the invention. Still other advantages of the invention may be realized by means of any of the instrumentalities, methods or combinations particularly pointed out in the Claims.

BRIEF DESCRIPTION OF THE DRAWINGS

Representative elements, operational features, applications and/or advantages of the present invention reside inter alia in the details of construction and operation as more fully hereafter depicted, described and claimed—reference being made to the accompanying drawings forming a part hereof, wherein like numerals refer to like parts throughout. Other elements, operational features, applications and/or advantages will become apparent to skilled artisans in light of certain exemplary embodiments recited in the Detailed Description, wherein:

Those skilled in the art will appreciate that elements in the Figures are illustrated for simplicity and clarity and have not necessarily been drawn to scale. For example, the dimensions of some of the elements in the Figures may be exaggerated relative to other elements to help improve understanding of various embodiments of the present invention. Furthermore, the terms 'first', 'second', and the like herein, if any, are used inter alia for distinguishing between similar elements and not necessarily for describing a sequential or chronological order. Moreover, the terms front, back, top, bottom, over, under, and the like in the Description and/or in the Claims, if any, are generally employed for descriptive purposes and not necessarily for comprehensively describing exclusive relative position. Skilled artisans will therefore understand that any of the preceding terms so used may be interchanged under appropriate circumstances such that various embodiments of the invention described herein, for example, are capable of operation in other orientations than those explicitly illustrated or otherwise described.

DETAILED DESCRIPTION OF EXEMPLARY EMBODIMENTS

The following descriptions are of exemplary embodiments of the invention and the inventors' conceptions of the best mode and are not intended to limit the scope, applicability or configuration of the invention in any way. Rather, the following description is intended to provide convenient illustrations for implementing various embodiments of the invention. As will become apparent, changes may be made in the function and/or arrangement of any of the elements described in the disclosed exemplary embodiments without departing from the spirit and scope of the invention.

Various representative implementations of the present invention may be applied to any system and/or method employing acoustic plate wave propagation. As used herein, the terms "fluid", "fluidic" and/or any contextual, variational or combinative referent thereof, are generally intended to include anything that may be regarded as at least being susceptible to characterization as generally referring to a gas, a liquid, a plasma and/or any matter, substance or combination of compounds substantially not in a solid or otherwise effectively immobile condensed phase. As used herein, the terms "inlet" and "outlet" are generally not used interchangeably. For example, "inlet" may generally be understood to comprise any cross-sectional area or component feature of a device, the flux through which tends to translate fluid from a volume element substantially external to the device to a volume element substantially internal to the device; whereas "outlet" may be generally understood as referring to any cross-sectional area or component feature of a device, the flux through which tends to translate fluid from a volume element substantially internal to the device to a volume element substantially external to the device. On the other hand, as used herein, the terms "liquid" and "gas" may generally be used interchangeably and may also be understood to comprise, in generic application, any fluid and/or any translationally mobile phase of matter. As used herein, the term "purged", as well as any contextual or combinative referent or variant thereof, is generally intended to include any method, technique or process for moving a volume element of fluid through the outlet of a device so as to dispose or otherwise positionally locate the "purged" volume element external to the device. Additionally, as used herein, the terms "valve" and "valving", as well as any contextual or combinative referents or variants thereof, are generally intended to include any method, technique, process, apparatus, device and/or system suitably adapted to control, affect or otherwise parameterize fluid flow scalar quantities (i.e., volume, density, viscosity, etc.) and/or fluid flow vector quantities (e.g., direction, velocity, acceleration, jerk, etc.). Additionally, as used herein, the terms "pump" and "pumping", or any contextual or combinative referents or variants thereof, are generally intended to include any method, technique, process, apparatus, device and/or system suitably adapted to flow or otherwise translate a fluid volume element from a first location to a second location. The term "monocrystalline", "epitaxial" or any contextual or combinative referents or variants thereof, are generally intended to refer to materials that are a substantially single crystal or that are effectively a single crystal to include materials having a relatively small number of defects such as dislocations and the like as are commonly found in substrates of silicon or germanium or mixtures of silicon and germanium and epitaxial layers of such materials.

A detailed description of an exemplary application, namely a system and method for flexural plate wave design and use is provided as a specific enabling disclosure that may be readily generalized by skilled artisans to any application of the disclosed system and method for acoustic actuation in accordance with various embodiments of the present invention. Moreover, skilled artisans will appreciate that the principles of the present invention may be employed to ascertain and/or realize any number of other benefits associated with acoustical actuation such as, but not limited to: improvement of pumping efficiency; improvement in valving efficiency; reduction of device weight; reduction of device form factor; improved sample loading in microfluidic assays; improvement in sample transport and throughput; microfluidic sample multiplexing and/or parallel sample processing; integration with micro-array techniques and/or systems; pumping of fuel and/or fuel components in a fuel cell system and/or device; chromatographic separations and any other applications now known or hereafter developed or otherwise described in the art.

FLEXURAL PLATE WAVE DEVICES

Flexural plate wave (also termed 'Lamb wave') devices are acoustic wave devices in which acoustic energy typically travels in a piezoelectric membrane with a thickness generally much less than the acoustic wavelength. The membrane generally deforms with relative large displacement normal to the membrane surface area. The plate wave may be initiated, for example, by piezoelectric transduction at an input interdigitated transducer (IDT). An output IDT spaced apart from the input IDT may be used to detect the wave and any frequency shift due, for example, to mass loading changes. FPW devices in accordance with various exemplary and representative aspects of the present invention may be employed as microfluidic pumps, filters, pressure sensors, density sensors, viscosity sensors and/or the like, or when coated with a film that is selective for an analyte of interest, to perform chemical and biological assays at parts per billion resolution. Representative applications include liquid and gas phase detection systems for chemical and biological agent detection for purposes of counter-terrorism and nonproliferation, small dosage in vivo drug release, sensing devices such as "artificial noses", virus/antibody detection devices, and on-chip cooling systems.

FPW sensors have been demonstrated to be more sensitive than SAW devices, in which Rayleigh waves typically travel on the surface of a bulk piezoelectric crystal. Performance of FPW devices is generally enhanced by a relatively higher coupling coefficient and thinner membrane dimensions. Accordingly, for example, a piezoelectric layer with an effectively high coupling coefficient and greatest mechanical strength is typically desired. A highly uniform membrane thickness may also be desired. In addition, a monolithic system with integrated control and sensor electronics may also be highly desirable for miniaturization, simplified packaging, reduced cost, inherent temperature compensation, reduced power consumption and/or the like. Monolithic integration with high speed compound semiconductor microelectronics and optoelectronics may be particularly well suited for high-performance, highly miniaturized sensors and microfluidic devices.

For thin film perovskite piezoelectrics like PZT, it may be desirable (in order inter alia to obtain maximal piezoelectric response) that spontaneous polarization of permanent dipoles in the perovskite occur substantially along a unitary axis. A superimposed DC bias may be required to pole polycrystalline PZT films, thereby fatiguing the film. In accordance with an exemplary embodiment of the present invention, an epitaxial or highly oriented film is disclosed. Additionally, membrane mechanical strength is often important for FPW devices. Thin polycrystalline piezoelectric films are generally inferior to monocrystalline films in this regard. For many of these reasons, a single crystal PZT film may comprise the most desirable material for FPW device fabrication in accordance with various representative aspects of the present invention.

An epitaxial PZT monocrystalline film offers substantially high piezoelectric coefficients as well as superior mechanical strength, which correspondingly allows relatively thin membranes for improved sensitivity and performance. The high thickness uniformity of an epitaxial layer may also be advantageous.

REPRESENTATIVE EXEMPLARY EMBODIMENTS

Figure 1:
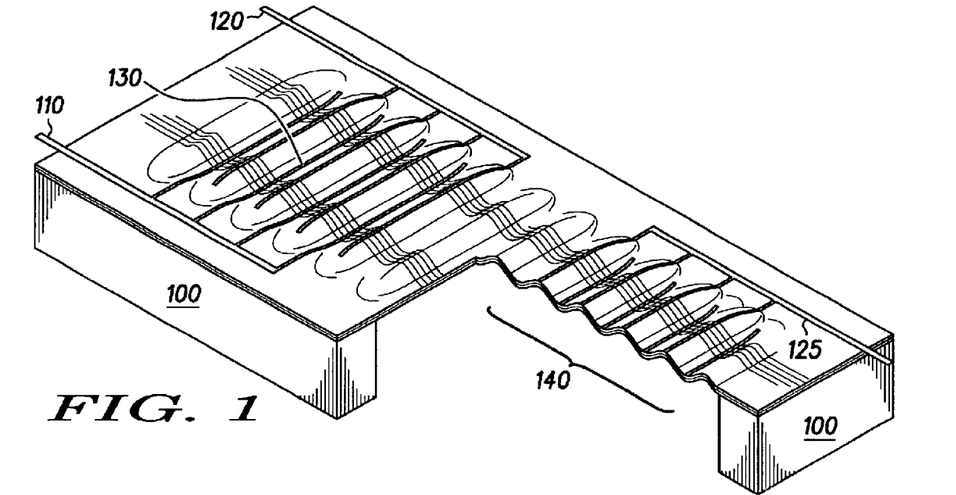
FIG. 1 representatively depicts a first view (isometric) of a flexural plate wave device in accordance with an exemplary embodiment of the present invention.

FIG. 1 representatively depicts a simplified isometric view of a flexural plate wave transducer mounted on a supporting substrate 100 in accordance with various exemplary aspects of the present invention. An input interdigitated electrode may be formed wherein a first terminal 110 and a second terminal 120 communicably couple interdigitated features 130 on, in or around acoustic membrane surface. An output interdigitated electrode may be similarly formed with a first terminal (not depicted in the cut-away section of FIG. 1) and a second terminal 125 communicably coupled to interdigitated features 140 on, in or around another portion of the acoustic membrane. Electrical actuation of the electrodes generally promotes oscillating plate modes within the membrane.

Figure 2:
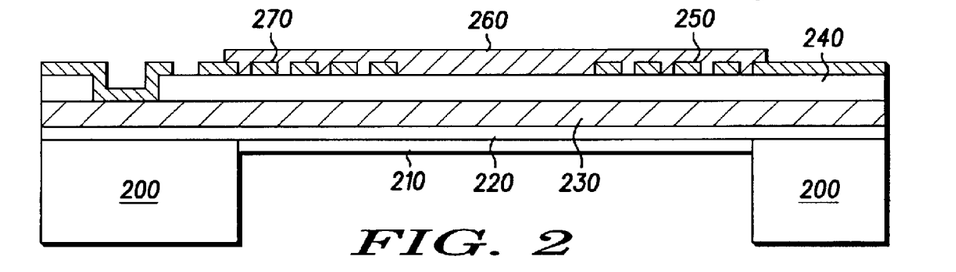
FIG. 2 representatively illustrates a second view (cutaway elevation) of a flexural plate wave device in accordance with an exemplary embodiment of the present invention.

FIG. 2 representatively depicts a simplified elevation view of a flexural plate wave transducer in accordance with another exemplary embodiment of the invention. Flexural plate wave devices of the present invention may include interdigitated input electrodes 270 and interdigitated output electrodes 250 that may be fabricated, for example, on a smooth surface of a substantially monocrystalline piezoelectric material 240 by inter alia depositing a thin film of metallic material such as aluminum, applying and patterning a photo-definable material and then etching the aluminum. Electrodes 270, 250 may be electrically coupled alternately to a first terminal (110 for interdigitated input electrode 270; first terminal for interdigitated output electrode not shown in the cut-away section of FIG. 1) and to a second terminal (120 for interdigitated input electrode 270; 125 for interdigitated output electrode 250). Electrodes 270, 250 may be typically periodic and/or parametric and define a characteristic acoustic wavelength and/or harmonic series at which flexural plate wave transducer may resonate at a characteristic center frequency upon application of electrical energy. Electrodes 270, 250 typically have a width that is substantially less than said characteristic acoustic wavelength and are spaced with a pitch that is also substantially less than said characteristic acoustic wavelength, although other designs are of course possible. Electrical stimulation in an appropriate range of frequencies applied to first and/or second terminals, and hence to the interdigitated features, results in acoustic plate waves generated within the flexural plate wave transducer, where such acoustic plate mode may be propagated outside of flexural plate wave transducer.

Flexural plate wave transducers, in accordance with various other representative aspects of the present invention, may also include: a monocrystalline silicon substrate 200; an amorphous oxide material layer 220; a monocrystalline perovskite oxide material layer 230; a monocrystalline piezoelectric material layer 240; an optional support layer 260 as well as flexural plate wave components previously described 250, 270. Monocrystalline piezoelectric material layer 240 may be formed over a monocrystalline perovskite oxide material 230 and an amorphous oxide material 220, both of which may be formed over a monocrystalline silicon substrate 200. In one embodiment of this example, monocrystalline piezoelectric material layer 240 can be formed on the monocrystalline perovskite oxide material 230.

As described earlier with reference to FIGS. 1 and 2, a flexural plate wave transducer may also comprise electrodes, which comprise at least two pluralities of electrodes interdigitated with each other, as illustrated for example in FIG. 1. Accordingly, electrodes may form a portion of an interdigitated transducer (IDT) to control the plate mode acoustic wave in monocrystalline piezoelectric material layer 240.

The electrodes may overlie a surface of monocrystalline piezoelectric material layer 240 or otherwise overlie portions of monocrystalline piezoelectric material layer 240. Electrodes may generally comprise any electrically conductive material whether now known or hereafter described in the art, such as a metal, that is compatible with acoustic plate wave applications. Preferably, electrodes may be comprised of the same electrically conductive material and may be fabricated substantially simultaneously with each other.

In one embodiment of a flexural plate wave transducer in accordance with an exemplary aspect of the present invention, the monocrystalline piezoelectric material layer 240 may be comprised of a ferroelectric material that can be poled. In a preferred exemplary embodiment, such poling may be accomplished by temporal application of direct current (DC) voltage to the interdigitated electrodes with respect to a ground potential at the bottom of a semiconducting monocrystalline substrate. Because the material for monocrystalline substrate is semiconducting, free charged carriers generally adjust so that an electrical field is formed across the ferroelectric material due to the application of the DC voltage. In some cases, the poling process may require the ferroelectric material to be heated to a poling temperature in the range of twenty-five to two hundred degrees Celsius, which may substantially reduce the time required to pole the ferroelectric material. The temperature may then be reduced substantially below the poling temperature, after which the DC voltage may be removed. In an embodiment where the substrate is n-type, a positive DC voltage is applied and the negatively charged carriers appear at the top surface of the semiconducting monocrystalline substrate. One skilled in the art will understand that a negative DC voltage could also be applied to the electrodes in certain situations. In another embodiment, the poling process would occur after the application of an aluminum film, but prior to patterning and etching of electrode features. In this case, the DC voltage would be applied to the whole metal thin film with respect to the backside of the semiconducting monocrystalline substrate and, after the poling process is completed, electrodes may then be photo-defined. This embodiment of the poling process may be advantageous inter alia for mass production of flexural plate wave transducers in accordance with the present invention.

As an example, flexural plate wave transducers can be a portion of a radio frequency (RF) acoustic wave device, the active portion of which may comprise, for example: (1) a first portion overlying a monocrystalline piezoelectric material layer; and (2) a second portion located in a monocrystalline piezoelectric material layer. The RF acoustic plate wave device can be a RF resonator and/or a RF acoustic wave filter. As an example, the RF acoustic wave filter can be a RF bandpass filter.

Flexural plate wave devices in accordance with various representative aspects of the present invention may also have a ladder-type configuration. Acoustic plate wave devices so designed may obtain the desired frequency response through electrical interconnection of acoustic plate wave transducers that are generally designed to resonate at particular characteristic frequencies. These resonances may exhibit themselves in their terminal impedance magnitude response as so-called poles and zeroes that are manipulated by known techniques to produce the desired filter response. This type of acoustic wave filter is advantageous for certain cellular telephone applications, but may be considered only one example of many possible acoustic plate wave filter configurations. For example, (1) the transducers comprising a ladder-type filter may include acoustic plate wave reflectors to improve their performance; (2) the acoustic plate wave filter may consist of interconnected transducers physically configured so that the acoustic plate mode energy is transmitted and/or received by other transducers, thus creating and employing acoustic plate wave tracks; (3) adjacent acoustic wave tracks may be coupled by various means to further improve or restrict their performance, including transverse acoustic coupling, electrical coupling, and reflective coupling, among others; (4) filters employing acoustic plate wave tracks may have their frequency response further refined by the use of acoustic wave reflectors that generally constrain the acoustic plate wave energy into regions known as cavities and may also use various coupler techniques that adjust the amount of energy coupled between cavities; and (5) acoustic plate wave filters may also include inputs and outputs that are electrically balanced or unbalanced.

In accordance with another embodiment of the invention, a flexural plate wave device may include an amorphous intermediate layer positioned between a substrate and, for example, an accommodating buffer layer. Such a device may also include a template layer between the accommodating buffer layer and a monocrystalline material layer. The template layer may be employed to help initiate growth of the monocrystalline material layer on the accommodating buffer layer. The amorphous intermediate layer generally helps to relieve strain in the accommodating buffer layer and by doing so, aids in the growth of a high crystalline quality accommodating buffer layer.

In accordance with yet another embodiment of the invention, a flexural plate wave device may further comprise a monocrystalline semiconductor or compound semiconductor wafer, preferably of relatively large diameter. The wafer may be of, for example, a material from Group IV of the periodic table. Examples of Group IV semiconductor materials include silicon, germanium, mixed silicon and germanium, mixed silicon and carbon, mixed silicon, germanium and carbon, and the like. Preferably the substrate may comprise a wafer containing silicon or germanium, and more preferably a high quality monocrystalline silicon wafer as typically used in the semiconductor industry. The substrate may also be, for example, silicon-on-insulator (SOI), where a thin layer of silicon is deposited or otherwise disposed substantially on top of an insulating material such as silicon oxide or glass. An accommodating buffer layer may preferably comprise a monocrystalline oxide or nitride material epitaxially grown, for example, on the underlying substrate. In accordance with yet another embodiment of the invention, an amorphous intermediate layer may be grown on a substrate at the interface between the substrate and the growing accommodating buffer layer by, for example, the oxidation of the substrate during the growth phase. The amorphous intermediate layer generally serves to relieve strain that might otherwise occur in the monocrystalline accommodating buffer layer as a result inter alia of differences in the lattice constants of the substrate and the buffer layer. As used herein, "lattice constant" generally refers to the distance between atoms of a cell measured in the plane of a surface. If such strain is not relieved by the amorphous intermediate layer, the strain may cause defects in the crystalline structure of the accommodating buffer layer. Defects in the crystalline structure of the accommodating buffer layer, in turn, could complicate achievement of a high quality crystalline structure in the monocrystalline material layer which may comprise, for example, a semiconductor material, a compound semiconductor material, a piezoelectric material or another type of material such as a metal or a non-metal.

The accommodating buffer layer may comprise, for example, a monocrystalline oxide or nitride material selected for its crystalline compatibility with the underlying substrate and with the overlying material layer. For example, the material may be an oxide or nitride having a lattice structure closely matched to the substrate and to the subsequently applied monocrystalline material layer. Materials that are suitable or otherwise adaptable to use for the accommodating buffer layer include metal oxides such as the alkaline earth metal titanates, alkaline earth metal zirconates, alkaline earth metal hafnates, alkaline earth metal tantalates, alkaline earth metal ruthenates, alkaline earth metal niobates, alkaline earth metal vanadates, alkaline earth metal tin-based perovskites, lanthanum aluminate, lanthanum scandium oxide, and other perovskite oxide materials, and gadolinium oxide. Additionally, various nitrides such as gallium nitride, aluminum nitride, and boron nitride may also be used for the accommodating buffer layer. Most of these materials are insulators, although strontium ruthenate, for example, is generally a conductor. Generally, these materials are metal oxides or metal nitrides, and more particularly, these metal oxides or nitrides typically include at least two different metallic elements. In some specific applications, the metal oxides or nitrides may include three or more different metallic elements.

The amorphous interface layer may comprise, for example, an oxide formed by the oxidation of the surface of the substrate and more preferably, may be composed of a silicon oxide. The thickness of the amorphous interface layer may be selected so as to be sufficient to relieve strain attributed to mismatches between the lattice constants of the substrate and the accommodating buffer layer. Typically, amorphous interface layer has a thickness in the range of approximately 0.5–5 nm.

The material for the monocrystalline material layer may be selected, as desired, for a particular structure or application. For example, the monocrystalline material may comprise a compound semiconductor which may be selected, as needed for a particular semiconductor structure, from any of the Group IIIA and VA elements (III–V semiconductor compounds), mixed III–V compounds, Group II (A or B) and VIA elements (II–VI semiconductor compounds), mixed II–VI compounds, Group IV and VI elements (IV–VI semiconductor compounds), mixed IV–VI compounds, Group IV elements (Group IV semiconductors), and mixed Group IV compounds. Representative examples include gallium arsenide (GaAs), gallium indium arsenide (GaInAs), gallium aluminum arsenide (GaAlAs), indium phosphide (InP), cadmium sulfide (CdS), cadmium mercury telluride (CdHgTe), zinc selenide (ZnSe), zinc sulfur selenide (ZnSSe), lead selenide (PbSe), lead telluride (PbTe), lead sulfide selenide (PbSSe), silicon (Si), germanium (Ge), silicon germanium (SiGe), silicon germanium carbide (SiGeC), and the like. However, the monocrystalline material layer may also comprise other semiconductor materials, metals, or non-metal materials which are used in the formation of various semiconductor structures, devices and/or integrated circuits.

Clearly, those embodiments specifically describing structures having compound semiconductor portions and Group IV semiconductor portions are meant to illustrate embodiments of the present invention and not limit the present invention. There are a multiplicity of other combinations and other embodiments of the present invention. For example, the present invention includes structures and methods for fabricating material layers which form semiconductor structures, devices and integrated circuits including other layers such as metal and non-metal layers. More specifically, the invention includes structures and methods for forming a compliant substrate which is used in the fabrication of semiconductor structures, devices and integrated circuits and the material layers suitable for fabricating those structures, devices, and integrated circuits. By using embodiments of the present invention, it is now simpler to integrate devices that include monocrystalline layers comprising semiconductor and compound semiconductor materials, as well as other material layers that are used to form those devices, with other components that work better or are easily and/or inexpensively formed within semiconductor or compound semiconductor materials. This allows a device to be shrunk, the manufacturing costs to decrease, and yield and reliability to increase.

In accordance with one embodiment of this invention, a monocrystalline semiconductor or compound semiconductor wafer can be used in forming monocrystalline material layers over the wafer. In this manner, the wafer is essentially a "handle" wafer used during the fabrication of semiconductor electrical components within a monocrystalline layer overlying the wafer. Therefore, electrical components can be formed within semiconductor materials over a wafer of at least approximately 200 millimeters in diameter and possibly at least approximately 300 millimeters.

By the use of this type of substrate, the relatively inexpensive "handler" wafer overcomes the fragile nature of wafers fabricated of monocrystalline compound semiconductor or other monocrystalline material by placing the materials over a relatively more durable and easy to fabricate base substrate. Therefore, an integrated circuit can be formed such that electrical components, and particularly active electronic devices, may be formed within or using the monocrystalline material layer even though the substrate itself may include a different monocrystalline semiconductor material. Fabrication costs for compound semiconductor devices and other devices employing non-silicon monocrystalline materials should decrease because larger substrates may be processed more economically and more readily compared to the relatively smaller and more fragile substrates (i.e., conventional compound semiconductor wafers).

The material for monocrystalline piezoelectric material layer 240 can be selected, as desired, for a particular structure or application. For example, the monocrystalline piezoelectric material of monocrystalline piezoelectric material layer 240 can consist of a lead-based perovskite material including, but not limited to, lead zirconate titanate (i.e., $Pb(Zr_xTi_{1-x})O_3$ where x is 0 to 1 and preferably 0.2 to 0.6, lead lanthanum zirconate titanate (i.e., $(Pb_zLa_{1-z})(Zr_xTi_{1-x})O_3$ where x is 0 to 1 and preferably 0.2 to 0.6 and z is 0 to 1 and preferably 0 to 0.2, and lead magnesium niobate—lead titanate (i.e., $PB\ (Mg_xNb_{1-x})O_3—PbTiO_3$) where x is 0 to 1 and preferably 0.2 to 0.4, can also consist of lithium niobate (i.e., $LiNbO_3$), lithium tantalate ($LiTaO_3$), barium titanate (i.e., $BaTiO3$), and gallium nitride (GaN) with or without magnesium doping, and can further consist of materials comprising any of these aforementioned materials. Suitable materials for a template layer, when present for example in a semiconductor structure, chemically bond to selected sites of the surface of an accommodating buffer layer and provide sites for the nucleation of the epitaxial growth of monocrystalline piezoelectric material layer 240.

The monocrystalline piezoelectric material of monocrystalline piezoelectric material layer 240 can have a Curie temperature of less than approximately one thousand degrees Celsius to make monocrystalline piezoelectric material layer 240 compatible with conventional semiconductor materials when a semiconductor structure is integrated onto the same semiconductor chip as a discrete semiconductor transistor or an integrated circuit. In one embodiment, the monocrystalline piezoelectric material of monocrystalline piezoelectric material layer 240 has a Curie temperature of less than or equal to approximately two hundred degrees Celsius. Also in this embodiment, the monocrystalline piezoelectric material of monocrystalline piezoelectric material layer 240 is a poled ferroelectric material. Accordingly, as used herein, the term "piezoelectric material" includes both inherently piezoelectric material and ferroelectric material that can be poled to exhibit piezoelectric characteristics.

REPRESENTATIVE FABRICATION TECHNIQUES

In one embodiment, monocrystalline piezoelectric layer 240 may be deposited or epitaxially grown using any suitable thin film deposition technique such as, for example, solution gelation (sol-gel), RF sputtering, metal organic deposition (MOD), MBE, CVD, MOCVD, MEE, ALE, PVD, CSD, PLD, or the like. The monocrystalline piezoelectric layer may be epitaxially deposited on monocrystalline perovskite oxide film 230, and may be epitaxially grown to a thickness of approximately 100 nm to several micrometers. After being deposited or epitaxially grown, the monocrystalline piezoelectric layer may be heated, preferably at a temperature less than or equal to the Curie temperature of the monocrystalline piezoelectric layer. The monocrystalline piezoelectric layer has a top surface and may be preferably comprised of a ferroelectric material. Thereafter, electrodes may be electrically shorted to each other, overlie the surface of the monocrystalline piezoelectric layer, and overlie first portions of the monocrystalline piezoelectric material. Then, a second plurality of electrodes may be formed which may be electrically shorted to each other, overlie the surface of the monocrystalline piezoelectric material, overlie second portions of the monocrystalline piezoelectric material, and are interdigitated with the electrodes of the previous step.

If the monocrystalline piezoelectric layer is comprised of a ferroelectric material, then it may be subsequently poled. The poling generally orients dipoles in the monocrystalline piezoelectric layer when the monocrystalline piezoelectric layer is comprised of a ferroelectric material. The poling process can be achieved, for example, by applying a DC voltage to the monocrystalline piezoelectric layer to produce a polarization pattern in the monocrystalline piezoelectric layer. More specifically, in an optional step, a first and second portion of the monocrystalline piezoelectric layer may be poled in a first direction. As an example, the first direction may be substantially perpendicular to the surface of the monocrystalline piezoelectric material. This may be performed by applying a DC voltage pulse to the first and second portions of the monocrystalline piezoelectric material at room temperature or a temperature of approximately twenty-five to two hundred degrees Celsius to polarize the first and second portions of the monocrystalline piezoelectric material in the first direction. The voltage pulse may be applied to the first and second portions of the monocrystalline piezoelectric material via the electrodes.

Accordingly, an improved integrated circuit having a flexural plate wave device and a process for fabricating the same is provided to overcome the disadvantages of the prior art. The integrated circuit has a high quality monocrystalline piezoelectric layer over a monocrystalline layer such as a semiconductor substrate. The high quality monocrystalline piezoelectric layer has a lower manufacturing cost compared to the prior art while still providing comparable, if not superior, flexural plate wave properties for acoustic wave propagation in the monocrystalline piezoelectric layer. A radio frequency or other high frequency output signal generated by the semiconductor component in the compound semiconductor layer and coupled to the flexural plate wave device is improved and confined. The integrated circuit reduces the number of components needed in, for example, a portable device and also reduces the size required in a portable device for such components, and further reduces the costs incurred in forming the individual components and assembling the same onto a circuit board. Examples of suitable portable devices include cellular telephones, wireless personal digital assistants (PDAs), two-way pagers, two-way radios and the like. The addition of optional CMOS control circuitry to the integrated circuit increases the functionality of the integrated circuit. A common silicon chip in a cellular telephone is a digital signal processor (DSP) commonly used to interpret a digital signal into voice or data. Therefore, the integrated circuits described herein may permit a single chip to transmit and/or receive a digital signal, interpret or de-construct the digital signal into an analog signal or vice versa, and output the signal, for example, to a speaker or an antenna.

REPRESENTATIVE CHROMATOGRAPHIC APPLICATIONS

In general, the majority of chemical analysis techniques are at best selective; few, if any, are actually specific. Consequently, the separation of analyte(s) from heterogeneous multi-component samples is often an important step in many analytical procedures. The most widely used conventional means of performing analytical separations are electrophoresis and chromatography—both comprising methods that find application in nearly every scientific discipline.

Column chromatography was invented and named by the Russian botanist Mikhail Tswett shortly after the turn of the $20^{th}$ Century. Tswett employed the technique to separate various plant pigments (e.g., chlorophylls and xanthophylls) by passing solutions of samples through a glass column packed with finely divided calcium carbonate. The separated solutes appeared as colored bands on the column, which accounts for the name Tswett gave for the technique from the Greek chroma meaning "color" and graphein meaning "to write".

Various chromatographic technologies have appeared in the last five decades, due not only to the development of several new types of methods but also to the growing need by engineers and scientists for better means for characterizing complex mixtures. The significant impact of these technologies may be demonstrated by the 1952 Nobel Prize awarded to Martin and Synge for their discoveries in the field of chromatography. Perhaps even more impressive are twelve Nobel Prize awards between the years of 1937 and 1972 that were based upon work substantially relying on various chromatographic techniques.

In general, chromatography comprises a diverse and important group of methods that permit separation of analyte components of complex mixtures, where many of these separations may be impossible or otherwise prohibitively difficult by other means. Typically, a sample is dissolved in a mobile phase, which may be a gas, a liquid or a super-critical fluid. The mobile phase is then forced through an immiscible stationary phase, which is fixed in place in either a column or on a solid surface. The two phases are chosen so that the components of the sample distribute themselves between the mobile and stationary phases to varying degrees. Those analyte components that are strongly retained by the stationary phase move slowly with respect to the flow of mobile phase. In contrast, analyte components that are weakly held by the stationary phase travel more rapidly. As a consequence of these differences in flow velocities (i.e., mobilities), analyte components separate into discrete bands that may be analyzed qualitatively and/or quantitatively. See, for example, E. Heftmann, *Chromatography. Fundamentals and Applications of Chromatography and Electrophotometric Methods,* 1983; P. Sewell and B. Clarke, *Chromatographic Separations,* 1988; J. A. Jonsson, *Chromatographic Theory and Basic Principles,* 1987; R. M. Smith, *Gas and Liquid Chromatography in Analytical Chemistry,* 1988; E. Katz, *Quantitative Analysis Using Chromatographic Techniques,* 1987; and J. C. Giddings, *Unified Separation Science,* 1991. In general, chromatography is typically divided into five broad categories based on the mechanism of interaction between solute analytes and the stationary phase of the chromatographic field: adsorption chromatography; partition chromatography; ion-exchange chromatography; molecular exclusion chromatography; and affinity chromatography.

Adsorption chromatography is generally regarded as the oldest form of chromatography and makes use of a solid stationary phase with a liquid or gaseous mobile phase. Solutes are usually adsorbed onto the surface of stationary phase particles, while equilibration between the stationary phase and the mobile phase accounts for separation of solute analytes.

Partition chromatography involves a liquid stationary phase formed on a thin film on the surface of a solid support. Solute equilibrates between the stationary liquid and the mobile phase. In adsorption and partition chromatography, a substantially continuous equilibration of solute between the mobile and stationary phases occurs. Columns may be packed with stationary phase or may be open tubular with stationary phase coated on the inner walls.

Ion-exchange chromatography utilizes anions (e.g., $SO_3^-$) or cations (e.g., $N(CH_3)_3^+$) that are covalently attached to the solid stationary phase (e.g., usually a resin) and the mobile phase is typically a liquid. Analyte solute ions of opposite charge are attracted to the stationary phase by coulombic forces.

Molecular exclusion chromatography (i.e., gel filtration -or- gel permeation chromatography) separates molecules by size, with larger analyte solutes passing through the chromatographic field more quickly than smaller ones. Unlike other forms of chromatography, there is generally no attractive interaction between the stationary phase and the analyte solute; rather, the liquid or gaseous mobile phase passes through a porous gel. The pores are generally small enough to exclude larger molecules, but not smaller ones. Smaller molecules usually take longer to pass through the column because they enter the gel pores and therefore must flow through a larger volume before leaving the column. In molecular exclusion chromatography, the fraction of stationary-phase volume available to solute generally decreases as the size of the solute molecules increase.

Affinity chromatography is generally believed to be the most selective type of chromatography—employing specific interactions between one kind of analyte molecule and a second covalently attached (i.e., immobilized) to the stationary phase. For example, the immobilized molecule may be an antibody to a particular protein. When a mixture containing, for example, several hundred proteins is passed through the chromatographic field, only the specific protein that reacts with the corresponding antibody will generally be bound to the column. After washing the remaining solutes from the column, the desired protein may thereafter be dislodged, for example, by changing the pH or ionic strength. Affinity chromatography generally relies on chemically specific, non-covalent interactions between the stationary phase and at least one analyte solute in a heterogeneous sample.

The speed of the mobile phase passing through a chromatographic field is expressed either as a volume flow rate or as a linear flow rate. Consider, for example, a liquid chromatography experiment in which the column has an inner diameter of 0.60 cm (radius r=0.30 cm) and the mobile phase occupies 20% of the column volume. Each centimeter of column length l has a volume corresponding to $\pi r^2 x l$; here 0.283 mL, of which 20% (i.e., 0.0565 mL) accounts for the mobile phase (i.e., the solvent system). The volume flow rate $$\left(e.g., \frac{mL}{min}\right)$$

expresses how much volume of solvent per unit time travels through the chromatographic field. The linear flow rate r $$\left(e.g., \frac{cm}{min}\right)$$

tells how many unit distances of column length are traveled per unit time by the solvent system. In the instant example, because 1 cm of column length contains 0.0565 mL of mobile phase, 0.3 mL would occupy $$\frac{0.3 \text{ mL}}{0.0565 \frac{\text{mL}}{\text{cm}}} = 5.3 \text{ cm}$$

of column length. Accordingly, the linear flow rate corresponding to $$0.3 \frac{\text{mL}}{\text{min}} \text{ is } 5.3 \frac{\text{cm}}{\text{min}}.$$

Analytes eluting from a chromatographic field may be observed with a variety of detectors, such as, for example: thermal conductivity detectors; flame ionization detectors; electron capture detectors; flame photometric detectors; alkali flame detectors; sulfur chemiluminescence detectors; atomic emission detectors and the like. The trace of the detector response as a function of elution time is known as a chromatogram. The retention time $t_r$ for each component is the time needed after injection of the sample onto the chromatographic field until the corresponding analyte is detected. Unretained mobile phase travels through the column in a minimum time $t_m$. The adjusted retention time $t'_r$ for a solute is the additional time required for analyte to travel the linear transport distance of the chromatographic field, beyond the time required by unretained solvent in accordance with $t'_r = t_r - t_m$.

The relative retention of two components is given as a quotient of the corresponding adjusted retention times. The capacity factor for a single component is the adjusted retention time divided by the elution time for the solvent. Capacity factor generally describes the ratio of time spent by solute in the stationary phase to time spent in the mobile phase. When scaling up from a small sample load to a large load, the cross-sectional area of the column is typically increased in proportion to the sample load while column length and linear flow rate are generally held constant.

For any two components 1 and 2, the relative retention $\alpha$ is defined as $$\alpha = \frac{t'_{r2}}{t'_{r1}}$$

where $t'_{r2} > t'_{r1}$, corresponding to $\alpha > 1$. The greater the relative retention, the greater the separation between the analyte components. Relative retention is generally independent of flow rate and can therefore be used to help identify peaks when the flow rate changes. For each peak in a chromatogram, the capacity factor k' is given as $$k' = \frac{t_r - t_m}{t_m};$$

which is to say that the capacity factor is the ratio of the time the solute spends in the stationary phase relative to the time the solute spends in the mobile phase. Accordingly, the longer a component is retained by the chromatographic field, the greater the capacity factor. This gives rise to the partition coefficient $$K = \frac{C_s}{C_m}$$

which corresponds to the ratio of solute concentration in the stationary phase $C_x$ relative to the concentration in the mobile phase $C_m$. Accordingly, the greater the ratio of partition coefficients between mobile and stationary phases, the greater the separation between two components of a mixture.

Given a chromatographic field of infinite permeability and cross-sectional area A that extends from x to x+l (where l represents the linear transport distance of the flow-path), the volume of the chromatographic field may be expressed as V=Al. Let the concentration at point x of analyte solute component G be [G] at time t. Accordingly, the number of particles that enter the chromatographic field per unit time is JA where J is the solute particle flux. Therefore, the rate of increase in molar concentration inside the chromatographic field due to the incoming particle flux is $$\left.\frac{\partial [G]}{\partial t}\right|_x = \frac{JA}{Al} = \frac{J}{l}.$$

Consider also an out-bound flux of solute particles at the x+l surface of the chromatographic field which may be similarly derived as $$\left.\frac{\partial [G]}{\partial t}\right|_{x+l} = \frac{J'A}{Al} = \frac{J'}{l}.$$

Therefore, the net time-rated change of concentration (i.e., the concentration velocity) may be expressed as:

$$\frac{d[G]}{dt} = \frac{J - J'}{l}$$

Suppose: (1) that the flux of solute particles J diffusing inside the chromatographic field comprises motion in response to a thermodynamic force $\mathscr{F}$ arising from a concentration gradient; (2) that the analyte particles reach a steady-state drift speed s when the thermodynamic force $\mathscr{F}$ is matched by the viscous drag; (3) that the drift speed s is proportional to the thermodynamic force; $\mathscr{F}$ (4) that the solute particle flux J is proportional to the drift speed; and (5) that the thermodynamic force $\mathscr{F}$ is proportional to the spatial concentration gradient $$\frac{d[G]}{dx}.$$

The resulting chain of proportionalities $J \propto s$, $s \propto \mathscr{F}$, and $$\mathscr{F} \propto \frac{d[G]}{dx}$$

implies that the solute particle flux J is proportional to the concentration gradient $$\frac{d[G]}{dx},$$

which will be apparent to skilled artisans as corresponding to 'Fick's First Law of Diffusion'. The constant of proportionality is given as the diffusion coefficient $\mathscr{D}$ in the equation $$J = \mathscr{D} \frac{d[G]}{dx}$$

for diffusion restricted to a single dimension x. Therefore, the expression J−J' taken from the expression for the diffusive concentration velocity becomes $$D\frac{d[G]}{dx} - D\frac{d[G]}{dx}.$$

Substitution of the linear accumulation of solute particle concentration over the length of the chromatographic field yields $$J - J' = \mathscr{D}\frac{d}{dx}\left([G] + \frac{d[G]}{dx}l\right) - \mathscr{D}\frac{d[G]}{dx}$$

which further reduces to $$J - J' = \mathscr{D}l\frac{d^2[G]}{dx^2}.$$

This expression may then be substituted back into the concentration velocity expression to give:

$$\frac{d[G]}{dt} = \frac{J - J'}{l} = \mathscr{D}\frac{d^2[G]}{dx^2} = \mathscr{D}\nabla_x^2 [G]$$

which will be apparent to skilled artisans as the time dependent diffusion equation according to 'Fick's Second Law of Diffusion' and relates the concentration velocity at any point to the spatial variation of the concentration at that point. More generally, this may be appreciated as a physical basis for the typically observed behavior of diffusing chemical species translating away from areas of relative high concentration to areas of relative lower concentration (i.e., "moving down the concentration gradient").

Next, consider the time dependence of the partial molecular pressure p of an eluting component G from a chromatographic field of given volume V. The 'Ideal Gas Law' PV=nRT, which for molecular-scale systems rather than for large aggregates of particles (e.g., moles of molecules), becomes pV=nkT wherein: p is the partial molecular pressure; V is the volume of the container providing spatial boundary conditions; n is the number of particles; k is the Boltzmann constant; and T is the temperature. Solving for the partial pressure yields $$p = \frac{nkT}{V}.$$

After taking the partial derivative with respect to time at constant temperature and volume, the following expression for the pressure velocity may be obtained:

$$\left(\frac{\partial p}{\partial t}\right)_{T,V} = \frac{\partial \left(\frac{nkT}{V}\right)}{\partial t} = \frac{kT}{V}\frac{\partial n}{\partial t}$$

For an eluting analyte solute that is not replenished over time as the solute escapes, the time-rated change of the number of solute particles is given as $$\frac{\partial n}{\partial t} = -Z_w A_o,$$

where $Z_w$ is the collisional frequency associated with the mean free path of the solute particles and $A_0$ is the area of the opening that the solute particles have available for elution from the chromatographic field. The collisional frequency is related to the partial pressure of the solute particles p, the mass of the particles m and the temperature of the system T by the equation $$Z_w = \frac{p}{\sqrt{2\pi m k T}}.$$

Substitution of this relation back into the expression for the pressure velocity yields $$\frac{\partial p}{\partial t} = \frac{-p A_0}{V} \sqrt{\frac{kT}{2\pi m}}$$

which integrates over time to $$p = p_0 e^{\frac{-t}{\tau}}$$

where $$\tau = \frac{V}{A_0} \sqrt{\frac{2\pi m}{kt}}.$$

From this expression for the pressure velocity, the following may generally be observed: (1) if the eluent (i.e., solvent and sample) is not replenished, the pressure decreases exponentially to zero; (2) the pressure velocity is faster with increasing temperature and slower with decreasing temperature; (3) the pressure velocity is slower with heavier solute particles and faster with less massive particles; (4) the pressure velocity is faster with increasing surface area of the chromatographic field and slower with decreased surface area; and (5) the pressure velocity is slower with increasing volume of the chromatographic field and faster with decreasing volume.

At constant temperature, the time derivative of the expression for the partial pressure $$p = \frac{nkT}{V}$$

becomes:

$$\left(\frac{\partial p}{\partial t}\right)_T = kT \frac{\partial \left(\frac{n}{V}\right)}{\partial t} = kT \frac{\partial [G]}{\partial t}$$

Therefore, substituting the expression corresponding to Fick's Second Law of Diffusion for the concentration velocity previously derived, the generalized expression for the pressure velocity of solute particles diffusing in three dimensions in a chromatographic field of infinite permeability as a function of concentration of the solute particles [G] may be represented as:

$$\left(\frac{dp}{dt}\right)_T = -kT\mathscr{D}_G \nabla^2 [G] = -kT\mathscr{D}_G \left(\frac{\partial^2}{\partial x^2} + \frac{\partial^2}{\partial y^2} + \frac{\partial^2}{\partial z^2}\right)[G].$$

if, however, the chromatographic field is assumed to have finite diffusive permeability (indeed, as generally required for achieving chromatographic separation), an additional diffusion coefficient $\hat{D}_{\Xi(a,b,c)}$ may be included to account for various permeability metrics such as, for example: the number of chromatographic theoretical plates, chromatographic plate height, stationary phase adsorption, non-uniform porosity; anisotropic transport along different dimensions; hydrophobicity; capillary defects; etc.

For example, consider the expression for a biomolecular component $\mathscr{B}$ diffusing through a chromatographic field (or otherwise porous barrier)$\Xi$:

$$\left(\frac{dp}{dt}\right)_{\Xi\mathscr{B}}^{diffusion} = -kT\left(\hat{D}_{\Xi(a,b,c)} \mathscr{D}_{\mathscr{B}}\right)\left(\frac{\partial^2}{\partial x^2} + \frac{\partial^2}{\partial y^2} + \frac{\partial^2}{\partial z^2}\right)[\mathscr{B}]$$

Upon inspection, this expression relates the concentration of the biomolecular component $\mathscr{B}$ at any point within the chromatographic field (or otherwise porous barrier) $\Xi$ to the three dimensional variation of biomolecular component $\mathscr{B}$ concentration at that point; which is to say that $\mathscr{B}$ will passively diffuse through a chromatographic field so as to move down its concentration gradient from volume elements comprising higher $\mathscr{B}$ concentration to volume elements comprising relative lower $\mathscr{B}$ concentration.

Substitution of $A_\Xi l$ for the volume V in the effusion equation $$\frac{dp}{dt} = \frac{-p A_0}{V} \sqrt{\frac{kT}{2\pi m}}$$

yields $$\frac{dp}{dt} = \frac{-p A_0}{A_\Xi l} \sqrt{\frac{kT}{2\pi m}}.$$

If the ratio of the area of the aggregate void-volume to the aggregate surface area of the chromatographic field is taken to be a dimensionless quantity $\theta$ corresponding to the porosity of the chromatographic field, a composite expression for elution of biomolecular component $\mathscr{B}$ becomes:

$$\left(\frac{dp}{dt}\right)_{\Xi\mathscr{B}}^{elution} = -p_\mathscr{B} \theta_\Xi \sqrt{\frac{kT}{2\pi m_\mathscr{B} l_\Xi^2}}$$

and relates the pressure of $\mathscr{B}$ that elutes through the chromatographic field (or otherwise porous barrier) $\Xi$ to: the back-side pressure of the biomolecular component $p_\mathscr{B}$; the temperature T; the mass of the biomolecular component $m_\mathscr{B}$; the linear transport distance of the chromatographic field l; and the porosity of the chromatographic field a $\theta_\Xi$.

Accordingly, the biomolecular analyte solute $\mathscr{B}$ will generally: (1) elute more rapidly at higher operating temperatures and more slowly at lower temperatures; (2) elute more rapidly with increased back-side pressure of $\mathscr{B}$ and more slowly with decreased back-side pressure; (3) elute more rapidly with chromatographic fields having increased porosity and more slowly with decreased porosity; and (4) elute more rapidly with porous chromatographic fields having decreased linear transport distances (i.e., shorter columns) and more slowly with increased transport distances.

Plate height $$H = \frac{\sigma^2}{x},$$

where σ is the standard deviation and x is the linear transport distance along the flow-path, is a measure of how well chromatographic bands of analyte solute may be separated on a particular chromatographic field. The number of plates for a Gaussian peak is generally given as $$N = 16\frac{t_r^2}{w^2},$$

where $t_r$ is the retention time and w is the peak width (typically taken as four standard deviations at the baseline; i.e., 4σ). Resolution of neighboring peaks becomes the difference in retention time divided by the average width w measured at the baseline. Resolution is proportional to $\sqrt{N}$ and also generally increases with relative retention and capacity factor. Accordingly, doubling the length of a chromatographic field generally increases resolution by a factor of approximately $\sqrt{2}$.

The standard deviation of a diffusing band of solute generally corresponds to $\sigma = \sqrt{2Dt}$, where D is the composite diffusion coefficient and t is time. The van Deemter equation describes band broadening on a chromatographic field as:

$$H \approx A + \frac{B}{u_x} + Cu_x$$

where H is the plate height, $u_x$ is the linear flow rate along the linear transport path of the chromatographic field, and A, B and C are constants: A representing irregular flow paths, B representing longitudinal diffusion and C representing the finite rate of transfer of analyte solute between mobile and stationary phases for a given column. The optimum flow rate, which generally minimizes plate height, is faster for gas chromatography than for liquid chromatography. The number of plates and the optimal flow rate usually increase as the stationary-phase particle size is decreased. Open tubular columns typically provide higher resolution and shorter analysis times than packed columns. In general, bands spread not only on the chromatographic field but also during sample injection as well as during component analyte detection. Overloading and tailing may be corrected by inter alia using smaller samples or by masking strong adsorption sites on the stationary phase. Additionally, there are several underlying processes that may impact the plate height, such as, for example: longitudinal diffusion; resistance to mass transfer in the mobile and/or stationary phase; and eddy diffusion.

To monitor the performance of a particular column, it is usually a recommended practice to periodically measure the capacity factor of a standard sample, the number of theoretical plates and/or peak asymmetry. Variations in any of these values generally indicate degradation of the chromatographic field over time and/or repeated use. As used herein, the term "chromatographic field" may be understood to include any system and/or method for electrophoretic separation as well.

Figure 3:
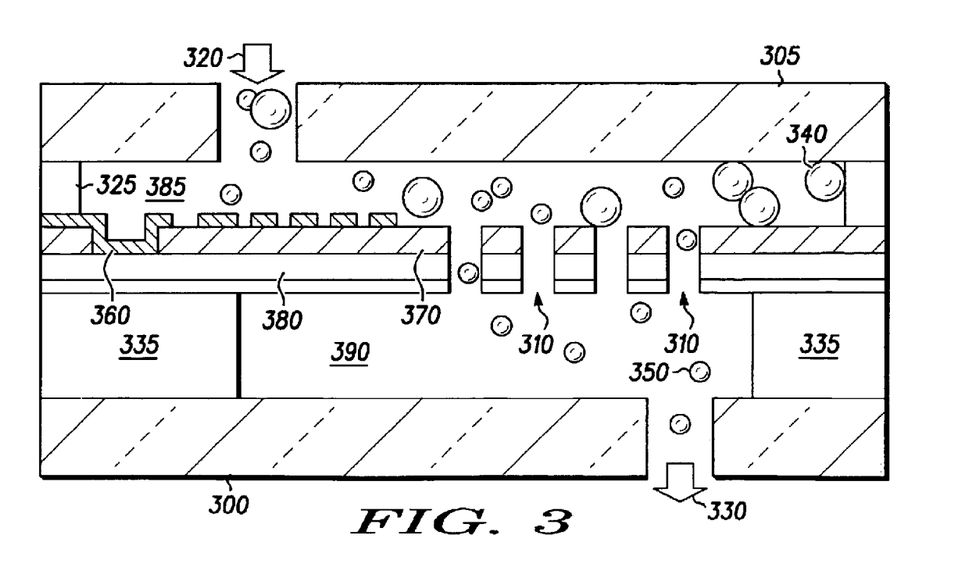
FIG. 3 representatively depicts a particle separation device employing a flexural plate wave agitator in accordance with yet another exemplary embodiment of the present invention.

As generally depicted, for example in FIG. 3, a flexural plate wave device for the separation of a mixture is disclosed in accordance with an exemplary embodiment of the present invention. A flexural plate wave device is disposed within a housing having a first surface 300, a second surface 305 and various support features 325, 335. The device further comprises a fluid inlet 320 and a fluid outlet 330. In general, the housing is typically otherwise effectively impermeable. A mixture, comprising at least two chemical components, enters inlet 320 where the mixture diffusively expands to fill inlet chamber 385. The flexural plate wave device generally comprises an interdigitated transducer 360, a monocrystalline piezoelectric membrane 370 and a monocrystalline perovskite material layer 380. As the flexural plate wave device is actuated, the chemical mixture is agitated to accelerate thermal translation of certain chemical species through openings 310 into outlet chamber 390. For example, smaller molecular species 350 may be accordingly separated from larger molecular species 340. Thereafter, the separated chemical component(s) may be purged from the device through outlet channel 330. Skilled artisans, however, will appreciate that various alternative embodiments in accordance with the present invention may be configured or otherwise optionally adapted for other pumping, valving and/or parametric chromatographic separation applications. Another embodiment, for example, may be particularly useful in biomedical pumping applications such as dialysis and arterial pumps where protein adsorption leading to thrombosis is often a major failure mechanism. The self-cleaning feature of the flexural plate wave device would be expected to minimize protein adsorption in the pump and adjacent tubing. Additionally, highly miniaturized, self-contained devices capable of rapidly performing chemical and biological chromatography and/or assays of liquids and gases at parts per billion resolution may be realized, for applications such as chemical and biological agent detection, DNA sequencing, virus/antibody detection, etc. Additionally, the present invention may also be adapted for various integrated micropumps for on-chip cooling systems or small dosage in vivo drug release and other biomedical applications.

REPRESENTATIVE SENSOR APPLICATIONS

In yet another exemplary embodiment, the present invention provides means for sensing properties of chemical species inter alia dissolved in a fluid, deposited onto a surface immersed in a fluid, or removed from a solid surface immersed in a fluid. The invention may be practiced in conjunction with adsorbing, absorbing, or plating a chemical species onto a acoustic plate wave device surface 210 (e.g., FIG. 2) or by desorbing, dissolving, or corroding a species from the device surface 210 into solution, or by monitoring the extent and nature of certain acoustical and/or electrical interactions.

A representative embodiment of a sensor device, in accordance with an exemplary aspect of the present invention, may be fabricated on a substantially monocrystalline piezoelectric substrate having a surface portion 210 which may be coated with a material providing enhanced selectivity and/or sensitivity to a particular solution species. In the case of corrosion and electro deposition sensors, the immersed region may be coated with, for example, a metal or other conductive electrode material to which electrical contact may be made for the purpose of monitoring and/or applying a potential or electric current during the process of corrosion or electro deposition. Variation in the concentration of species on the device surface 210 may be detected inter alia via perturbations of acoustic plate mode waves propagating through the crystal having in-plane displacements at the surface-fluid interface.

The sensitivity of such detection and monitoring devices for sensing chemical species in fluids may depend on the use of appropriate acoustic modes. The optimal mode in accordance with various exemplary embodiments of the present invention comprises at least one—or alternatively, at least a superposition of more than one—acoustic plate modes. The acoustic plate modes generally propagate efficiently in the presence of fluids due inter alia to the absence of surface-normal components of particle displacement.

Association of particle masses to either surface of the acoustic plate mode sensor generally slows the velocity of the acoustic wave relative to that of the unperturbed substrate. Conversely, if mass is initially added to either device surface (i.e., in the form of a thin film), subsequent removal of a fraction or all of said mass typically causes the wave velocity to increase; the velocity reaching its unperturbed value when substantially all of the added mass has been removed. Additionally, changes in the mechanical properties (including, for example: stiffness; elasticity; and shear modulus) of a thin film in substantially direct contact with the acoustic plate mode sensor surface 210, generally produce perturbations of the acoustic wave velocity. Such variation in wave velocity resulting from change in surface mass and/or surface mechanical properties is analogous to that exhibited by conventional SAW sensors operating in contact with, for example, gas phase particles. The difference in the case of this invention is that these mass and mechanical changes may be more readily measured while the device is in substantially direct contact with a liquid, a measurement not easily performed with a Rayleigh wave device.

While the acoustic plate mode sensor is in contact with an analyte fluid, a fractional change in the velocity of the acoustic plate modes may result from changes in sensor surface conditions including inter alia changes in the characteristics of the sensor surface 210 or a thin film of material upon said sensor surface due to adsorption, absorption, deposition, removal, desorption or other mechanism involving disposition of matter whether now known or otherwise hereafter described in the art; or changes in the mechanical properties of a thin film or of the sensor surface itself.

An exemplary technique for measuring fractional velocity changes may include inter alia a radio frequency signal source driving an input transducer through an impedance matching transformer in order to propagate acoustic plate modes from the input transducer to an output transducer. The output transducer may be terminated through another matching transformer by, for example, a resistive load. A vector voltmeter or phase-sensitive meter equipped with at least two probes may be adapted to monitor the phase difference between the acoustic wave incident upon the input transducer and that received by the output transducer, thereby providing a measure of the perturbations in wave velocity. The probes may also be coupled to their respective signals through directional couplers.

Another measurement technique, in accordance with another exemplary embodiment, may include an output transducer connected to an input transducer through an amplifier suitably adapted for operation at certain radio frequencies. A directional coupler may be employed to direct a fraction of the power incident on the input transducer, for example, to a frequency counter which may alternatively provide another measure of the perturbations in wave velocity.

The input transducer, with periodicity d on substrate of thickness b, efficiently excites a family of acoustic shear plate modes whose frequency spectrum may be approximated by:

$$f_n = \frac{v_0}{2\pi}\sqrt{\left(\frac{2\pi}{d}\right)^2 - \left(\frac{n\pi}{b}\right)^2}$$

in which $v_0$ is the velocity of the acoustic wave propagating in a solid in the absence of bounding surfaces (5100 m/s for ST-quartz) and n is any integer. When the number N of finger pairs of the interdigitated features comprising the transducers is chosen such that $$N > 4\left(\frac{b}{d}\right)^2,$$

the bandwidth of the transducers will be sufficiently narrow such that each acoustic plate mode may generally be excited and detected individually; otherwise, a superposition of more than one plate mode will be excited and subsequently detected.

Acoustic plate modes may be used to measure the mass and mechanical properties of material present upon sensor surface 210, or deposited from (or removed to) a fluid in substantially direct contact with the sensing surface. Perturbations in acoustic plate mode wave velocities generally depend both on changes in surface mass and stiffness properties, with the fractional velocity perturbation represented, for example by:

$$\frac{\Delta v}{v_0} = -c_m \delta_m + F(K, \mu)$$

in which $c_m$, the mass sensitivity factor of the device, is given approximately by $$\frac{v_0^2}{c'b},$$

where $v_0$ is the unperturbed operating velocity and $c^\dagger$ is a stiffness parameter for the plate material; $\delta_m$ is the accumulated mass per unit area; and F is a function of the bulk modulus K and shear modulus $\mu$ of material on the sensing surface.

When the wave velocity in any layer accumulating on or present on the sensor surface is much less than the wave velocity in the sensor substrate, this accumulation layer and any changes in it will have a negligible effect on the acoustic wave velocity via mechanical properties. This, in turn, reduces the fractional velocity perturbation expression to the simpler form:

$$\frac{\Delta v}{v_0} = -c_m \delta_m$$

In this case, the fractional change in velocity, and thus oscillation frequency, is generally linearly proportional to changes in surface mass. A convenient and more precise way to monitor wave velocity may be to incorporate the acoustic plate device, in accordance with various exemplary aspects of the present invention, as a feedback element in an oscillator loop. The oscillation frequency of such a loop may be adapted to track and to be linearly proportional to the acoustic wave velocity, so that fractional changes in the latter may be measured with substantially improved accuracy. The fractional change in frequency may be thereby correlated to the fractional change in velocity given in the expressions vide supra times the fraction of acoustic plate mode propagation paths which experience a change in mass and/or mechanical properties. The signal represented by this treatment generally adds to the shift (i.e., additive constant) arising from, for example, the entrainment of liquid through viscous coupling. The acoustic plate mode sensitivity may generally be greatest when b, the plate thickness, is minimized.

In the foregoing specification, the invention has been described with reference to specific exemplary embodiments; however, it will be appreciated that various modifications and changes may be made without departing from the scope of the present invention as set forth in the claims below. The specification and figures are to be regarded in an illustrative manner, rather than a restrictive one and all such modifications are intended to be included within the scope of the present invention. Accordingly, the scope of the invention should be determined by the claims appended hereto and their legal equivalents rather than by merely the examples described above. For example, the steps recited in any method or process claims may be executed in any order and are not limited to the specific order presented in the claims. Additionally, the components and/or elements recited in any apparatus claims may be assembled or otherwise operationally configured in a variety of permutations to produce substantially the same result as the present invention and are accordingly not limited to the specific configuration recited in the claims.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components of any or all the claims.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted by those skilled in the art to specific environments, manufacturing specifications, design parameters or other operating requirements without departing from the general principles of the same.

We claim:

1. An apparatus comprising:
a monocrystalline silicon substrate;
an amorphous oxide material overlying the monocrystalline silicon substrate;
a monocrystalline perovskite oxide material overlying the amorphous oxide material;
a monocrystalline piezoelectric material overlying the monocrystalline perovskite oxide material; and
a flexural plate wave device located at least one of in, over and on the monocrystalline piezoelectric material.

2. The apparatus of claim 1 further comprising:
a monocrystalline compound semiconductor material located in at least one of:
under the monocrystalline piezoelectric material; over the monocrystalline piezoelectric material; in the monocrystalline piezoelectric material;
and adjacent to the monocrystalline piezoelectric material.

3. The apparatus of claim 1 further comprising:
a silicon semiconductor component located at least one of in, over and on the monocrystalline silicon substrate; and
an interconnect structure coupling the silicon semiconductor component and the flexural plate wave device.

4. The apparatus of claim 2 further comprising:
a silicon semiconductor component located at least one of in, over and on the monocrystalline silicon substrate; and
an interconnect structure coupling the silicon semiconductor component and the flexural plate wave device.

5. The apparatus of claim 2 further comprising:
a compound semiconductor component located in the monocrystalline compound semiconductor material; and
an interconnect structure coupling the compound semiconductor component and the flexural plate wave device.

6. The apparatus of claim 1 wherein:
the monocrystalline silicon substrate has a recess; and
the monocrystalline piezoelectric material is located in the recess.

7. The apparatus of claim 6 wherein:
the monocrystalline compound semiconductor material is located in at least one of:
under the monocrystalline piezoelectric material; over the monocrystalline piezoelectric material; and adjacent to the monocrystalline piezoelectric material.

8. The apparatus of claim 2 wherein:
the monocrystalline silicon substrate has a recess; and
the monocrystalline compound semiconductor material is located in the recess.

9. An apparatus comprising:
a monocrystalline silicon substrate;
an amorphous oxide layer overlying the monocrystalline silicon substrate;
a monocrystalline perovskite oxide layer overlying the amorphous oxide layer;
a monocrystalline ferroelectric and piezoelectric layer overlying the monocrystalline perovskite oxide layer; and
a flexural plate wave device located in and over the monocrystalline ferroelectric and piezoelectric layer.

10. The integrated circuit of claim 9 further comprising:
a plurality of silicon semiconductor components located in and over the monocrystalline silicon substrate; and
an interconnect structure electrically coupling together the plurality of silicon semiconductor components and the flexural plate wave device.

11. The integrated circuit of claim 9 wherein:
the monocrystalline silicon substrate has a recess; and
the monocrystalline ferroelectric and piezoelectric layer is located in the recess.

12. The integrated circuit of claim 9 further comprising:
a monocrystalline compound semiconductor layer at least one of:
overlying the monocrystalline perovskite oxide layer; underlying the monocrystalline perovskite oxide layer; and adjacent to the monocrystalline perovskite oxide layer.

13. The integrated circuit of claim 12 wherein:

the monocrystalline silicon substrate has a recess; and the monocrystalline compound semiconductor layer is located in the recess.

14. The integrated circuit of claim 13 wherein:

the monocrystalline silicon substrate has a first surface;

the recess is located in the first surface;

the monocrystalline compound semiconductor layer has a second surface; and the second surface is substantially planar with the first surface.

15. The integrated circuit of claim 13 wherein:

the monocrystalline silicon substrate has a different recess; and the monocrystalline ferroelectric and piezoelectric layer is located in said different recess.

16. The integrated circuit of claim 15 wherein:

the monocrystalline silicon substrate has a first surface;

the recess and the different recess are located in said first surface;

the monocrystalline ferroelectric and piezoelectric layer has a second surface:

the monocrystalline compound semiconductor layer has a third surface; and said first, second, and third surfaces are substantially planar with each other.

17. The integrated circuit of claim 16 further comprising:

a plurality of compound semiconductor components located in the compound semiconductor layer; and an interconnect structure electrically coupling together the plurality of compound semiconductor components and the flexural plate wave device.

* * * * *